United States Patent
Kato et al.

(10) Patent No.: US 9,249,453 B2
(45) Date of Patent: Feb. 2, 2016

(54) METHOD FOR IDENTIFYING A MALODOR INHIBITOR

(75) Inventors: Aya Kato, Utsunomia (JP); Naoko Saito, Utsunomiya (JP)

(73) Assignee: Kao Corporation, Tokyo (JP)

( * ) Notice: Subject to any disclaimer, the term of this patent is extended or adjusted under 35 U.S.C. 154(b) by 57 days.

(21) Appl. No.: 14/118,414

(22) PCT Filed: Jun. 5, 2012

(86) PCT No.: PCT/JP2012/064862
§ 371 (c)(1),
(2), (4) Date: Nov. 18, 2013

(87) PCT Pub. No.: WO2012/169644
PCT Pub. Date: Dec. 13, 2012

(65) Prior Publication Data
US 2014/0186864 A1    Jul. 3, 2014

(30) Foreign Application Priority Data
Jun. 6, 2011    (JP) .................................. 2011-126637

(51) Int. Cl.
*C12Q 1/68*        (2006.01)
*C12Q 1/66*        (2006.01)
(Continued)

(52) U.S. Cl.
CPC .............. *C12Q 1/66* (2013.01); *G01N 33/5058* (2013.01); *G01N 33/566* (2013.01); *G01N 2333/726* (2013.01); *G01N 2500/00* (2013.01)

(58) Field of Classification Search
CPC ................... G01N 2333/726; G01N 2500/00; G01N 33/5058; G01N 33/566; C12Q 1/66
See application file for complete search history.

(56) References Cited

U.S. PATENT DOCUMENTS

| 5,272,135 A | 12/1993 | Takruri |
| 7,585,833 B2 | 9/2009 | Fadel et al. |

(Continued)

FOREIGN PATENT DOCUMENTS

| JP | 11-241089 A | 9/1999 |
| JP | 2002-153545 A | 5/2002 |

(Continued)

OTHER PUBLICATIONS

Alignment performed by NCBI protein BLAST between instant Seq Id No. 4 and Prior art (Han) Seq Id No. 44 on May 18, 2015.*

(Continued)

*Primary Examiner* — Reza Ghafoorian
(74) *Attorney, Agent, or Firm* — Sterne, Kessler, Goldstein & Fox P.L.L.C.

(57) ABSTRACT

Provided is a method for identifying a malodor inhibitor based on a response of an olfactory receptor. The present invention provides a method for identifying a malodor inhibitor including: adding a test substance and a malodor-causing substance to at least one olfactory receptor selected from the group consisting of OR5P3, OR5K1, OR2W1, OR8H1, and a polypeptide which has 80% or more identity in amino acid sequence to any one of the aforementioned polypeptides; measuring the response of the olfactory receptor to the malodor-causing substance; identifying the test substance which can suppress the response of the olfactory receptor based on the measured response; and selecting, as a malodor inhibitor, the test substance which can suppress the response of the olfactory receptor.

17 Claims, 5 Drawing Sheets

(51) Int. Cl.
   G01N 33/50        (2006.01)
   G01N 33/566       (2006.01)

(56) References Cited

U.S. PATENT DOCUMENTS

| | | | |
|---|---|---|---|
| 9,057,090 | B2 | 6/2015 | Kato et al. |
| 2003/0207337 | A1* | 11/2003 | Han et al. ............... 435/7.2 |
| 2006/0293174 | A1 | 12/2006 | Hashizume et al. |
| 2007/0065394 | A1 | 3/2007 | Pinney |
| 2008/0032913 | A1 | 2/2008 | Finke et al. |
| 2008/0299586 | A1 | 12/2008 | Han et al. |
| 2009/0010958 | A1 | 1/2009 | Pinney |
| 2013/0210022 | A1 | 8/2013 | Kato et al. |
| 2013/0210775 | A1 | 8/2013 | Kato et al. |
| 2013/0216492 | A1 | 8/2013 | Kato et al. |

FOREIGN PATENT DOCUMENTS

| | | | |
|---|---|---|---|
| JP | 2003-024423 | A | 1/2003 |
| JP | 2003-24423 | A | 1/2003 |
| JP | 2003-137758 | A | 5/2003 |
| JP | 2005-296169 | A | 10/2005 |
| JP | 2005-325055 | A | 11/2005 |
| JP | 2008-136841 | A | 6/2008 |
| JP | 2012-050411 | A | 3/2012 |
| JP | 2012-050781 | A | 3/2012 |
| WO | WO 2005/007287 | A1 | 1/2005 |
| WO | WO 2005/046632 | A2 | 5/2005 |
| WO | WO 2012/029922 | A1 | 3/2012 |
| WO | WO 2013/119312 | A1 | 8/2013 |
| WO | WO 2013/171535 | A2 | 11/2013 |

OTHER PUBLICATIONS

International Search Report (ISR) for PCT/JP2012/064862; I.A. fd: Jun. 5, 2012, mailed Sep. 7, 2012 from the European Patent Office, Rijswijk, Netherlands.

International Preliminary Report on Patentability (IPRP), Chapter I of the Patent Cooperation Treaty, including the Written Opinion for PCT/JP2012/064862; I.A. fd: Jun. 5, 2012 issued Dec. 10, 2013, by the International Bureau of WIPO, Geneva, Switzerland.

Zhuang, H. et al., "Synergism of Accessory Factors in Functional Expression of Mammalian Odorant Receptors," J. Biol. Chem., May 2007; 282: 15284-15293, Am. Soc. Biochem. Mol. Biol., Baltimore, MD.

International Search Report (ISR) and Written Opinion for related appln PCT/US2012/067889; I.A. fd: Dec. 5, 2012, mailed Mar. 6, 2013 from the European Patent Office, Rijswijk, Netherlands.

Malnic, B et al., "The human olfactory receptor gene family," Proc Natl Acad Sci USA, Feb. 2004; 101: 2584-2589, National Academy of Sciences, Washington, DC.

Malnic, B., "Searching for the ligands of odorant receptors," Mol Neurobiol, Apr. 2007, 35:175-181, Humana Press, Clifton, NJ.

International Search Report and Written Opinion for PCT/IB2012/003131; I.A. fd: Dec. 29, 2012, mailed Feb. 13, 2014, by the European Patent Office, Rijswijk, Netherlands.

Database Caplus[Online], Chemical Abstracts Service, Columbus, Ohio, US; Kawasaki, Kiyomitsu:"Odor masking compositions containing fragrant substances for hair cosmetics", XP002719480,retrieved from STN, Database accession No. 2003:371661 abstract for JP 2003-137758 A.

Database Caplus[Online], Chemical Abstracts Service, Columbus, Ohio, US; Jan. 28, 2003, K. Shimazaki et al.: "Alkylpyrazine-odor-blocking agents containing pyrazines", XP002719444, retrieved from STN, Database accession No. 138:105972 abstract for JP 2003-024423 A.

Hindenlang David M, et al., "Reducing Odiferous Volatiles with Zeolites," Cosmetics & Toiletries, vol. 123, No. 7, Jul. 1, 2008, pp. 67, 68, 70-72 and 74, Wheaton, IL, US.

Oka, Y. et al., "The identification of the sense of smell receptor antagonist and physiologic significance," A collection of the Japan Society for Bioscience, Biotechnology and Agrochem 2003 meeting lecture subject matter, Mar. 5, 2003, p. 152, abstract #3A04p18, Yokohama, Japan.

Oka, Y et al., Olfactory receptor antagonism between odorants, EMBO J., Jan. 2004; 23(1):120-126, IRL Press, Oxford, England.

Saito, H. et al., "Odor coding by a mammalian receptor repertoire," Sci. Signal, 2009, 2(60), ra9, 28 pp., doi:10.1126/scisigna12000016, American Association for the Advancement of Science, Washington, DC.

Sanz, G et al., "Comparison of Odorant Specificity of Two Human Olfactory Receptors from Different Phylogenetic Classes and Evidence for Antagonism," Chem Senses, Jan. 2005; 30:69-80, IRL Press, Oxford, England.

Imahori, K. et al., "Skatole," in Biochemistry Dictionary, Mar. 1, 2000, $3^{rd}$ edition, $4^{th}$ printing, pp. 726-727, ISBN 4-8079-0480-9,Tokyo Chemistry Coterie Co., Ltd. (Tokyo Kagaku Dojin), Tokyo, Japan.

Touhara, K et al., "Function of the sense of smell receptor—Expression and function of the olfactory receptor gene superfamily," Igaku No Ayumi, vol. 212, No. 1, pp. 77-81, Jan. 1, 2005, lshiyaku Pub. Inc., Tokyo, Japan.

Excerpted file history (through Jul. 6, 2015) of U.S. Appl. No. 13/693,178, filed Dec. 4, 2012.

Excerpted file history (through May 27, 2015), U.S. Appl. No. 13/693,295, filed Dec. 4, 2012.

Shimazaki, K et al., "Evaluation of the odor activity of pyrazine derivatives using structural and electronic parameters derived from conformational study by molecular mechanics (MM3) and *ab initio* calculations," J Mol Structure (2005) 749:169-176, Elsevier, Netherlands.

* cited by examiner

Fig. 2
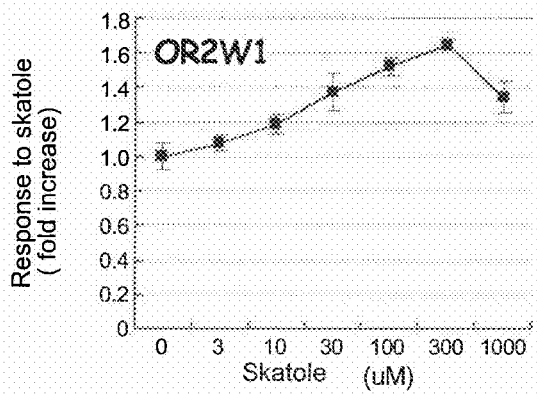
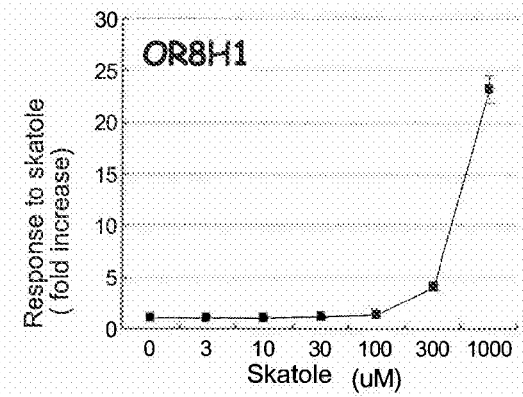
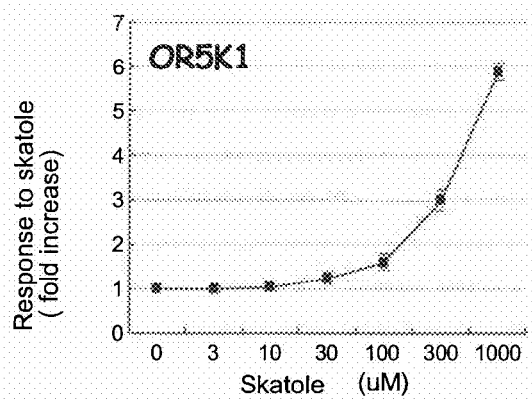
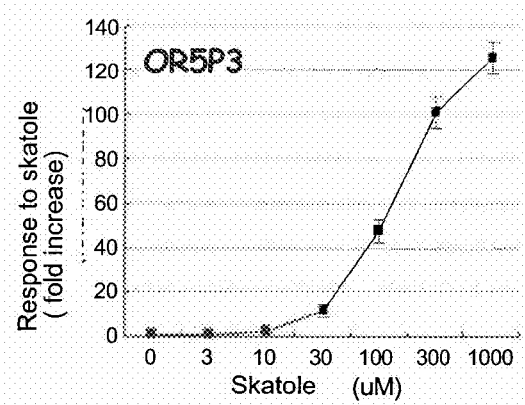

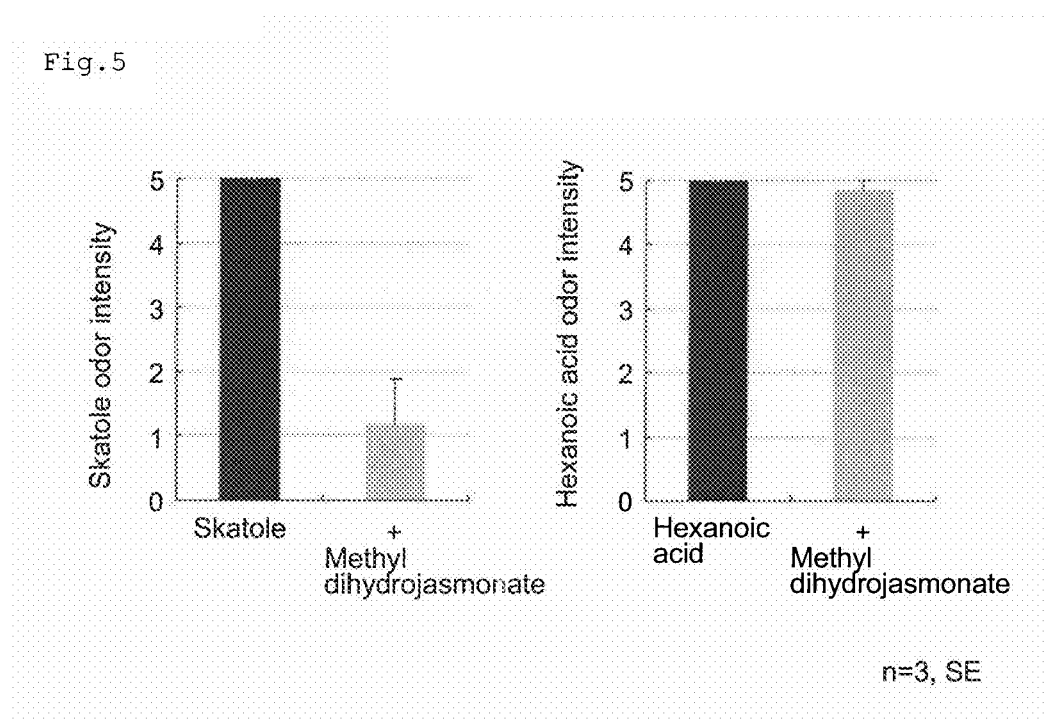

SEQUENCE LISTING

<160> NUMBER OF SEQ ID NOS: 11

<210> SEQ ID NO 1
<211> LENGTH: 963
<212> TYPE: DNA
<213> ORGANISM: Homo sapiens

<400> SEQUENCE: 1

```
atggaccaaa gcaattatag ttctttacat ggttttattc tgcttggctt ctctaaccat      60
ccaaaaatgg agatgatcct gtcaggagtt gtcgccatct tctacttaat tacattggtg     120
ggtaacacag ccatcattct tgcatctctc ctggattccc agcttcatac accaatgtac     180
tttttcctca gaaatttatc tttcctagat ctatgtttca caaccagcat catccctcag     240
atgctggtca acttgtgggg acctgataag accatcagct atgtgggttg tatcatccaa     300
ctctatgttt acatgtggtt gggctcagtt gagtgccttc tcctggctgt tatgtcctat     360
gatcgtttta cagctatatg taagcccttg cattattttg tagtcatgaa cccacatcta     420
tgtctaaaga tgattatcat gatctggagt attagtttgg ccaattctgt agtattatgt     480
acactcactc tgaatttgcc acatgtgga  aacaacattc tggatcattt cttgtgtgag     540
ttgccagctc tggtcaagat agcttgtgta gacaccacaa cagttgaaat gtctgttttc     600
gctttaggca ttataattgt cctcacacct ctcatcctta ttcttatatc ctatggctac     660
attgccaaag ctgtgctgag aacgaagtca aaagcaagcc agcgaaaagc aatgaatacc     720
tgtggatctc atcttactgt agtgtctatg ttctatggaa ctattatcta catgtacctg     780
caaccaggta cagggcttc  caaagaccag ggcaagttcc tcaccctctt ttacaccgtc     840
atcactccaa gtctcaaccc gctcatttac accttaagaa ataaggacat gaaggatgcc     900
ctgaagaaac tgatgagatt tcaccacaaa tctacaaaaa taaagaggaa ttgcaagtca     960
tag                                                                   963
```

<210> SEQ ID NO 2
<211> LENGTH: 320
<212> TYPE: PRT
<213> ORGANISM: Homo sapiens

<400> SEQUENCE: 2

```
Met Asp Gln Ser Asn Tyr Ser Ser Leu His Gly Phe Ile Leu Leu Gly
1               5                   10                  15

Phe Ser Asn His Pro Lys Met Glu Met Ile Leu Ser Gly Val Val Ala
            20                  25                  30

Ile Phe Tyr Leu Ile Thr Leu Val Gly Asn Thr Ala Ile Ile Leu Ala
        35                  40                  45

Ser Leu Leu Asp Ser Gln Leu His Thr Pro Met Tyr Phe Phe Leu Arg
    50                  55                  60

Asn Leu Ser Phe Leu Asp Leu Cys Phe Thr Thr Ser Ile Ile Pro Gln
65                  70                  75                  80

Met Leu Val Asn Leu Trp Gly Pro Asp Lys Thr Ile Ser Tyr Val Gly
                85                  90                  95

Cys Ile Ile Gln Leu Tyr Val Tyr Met Trp Leu Gly Ser Val Glu Cys
            100                 105                 110

Leu Leu Leu Ala Val Met Ser Tyr Asp Arg Phe Thr Ala Ile Cys Lys
        115                 120                 125

Pro Leu His Tyr Phe Val Val Met Asn Pro His Leu Cys Leu Lys Met
    130                 135                 140
```

```
Ile Ile Met Ile Trp Ser Ile Ser Leu Ala Asn Ser Val Val Leu Cys
145                 150                 155                 160

Thr Leu Thr Leu Asn Leu Pro Thr Cys Gly Asn Asn Ile Leu Asp His
                165                 170                 175

Phe Leu Cys Glu Leu Pro Ala Leu Val Lys Ile Ala Cys Val Asp Thr
            180                 185                 190

Thr Thr Val Glu Met Ser Val Phe Ala Leu Gly Ile Ile Val Leu
        195                 200                 205

Thr Pro Leu Ile Leu Ile Leu Ile Ser Tyr Gly Tyr Ile Ala Lys Ala
        210                 215                 220

Val Leu Arg Thr Lys Ser Lys Ala Ser Gln Arg Lys Ala Met Asn Thr
225                 230                 235                 240

Cys Gly Ser His Leu Thr Val Val Ser Met Phe Tyr Gly Thr Ile Ile
                245                 250                 255

Tyr Met Tyr Leu Gln Pro Gly Asn Arg Ala Ser Lys Asp Gln Gly Lys
                260                 265                 270

Phe Leu Thr Leu Phe Tyr Thr Val Ile Thr Pro Ser Leu Asn Pro Leu
                275                 280                 285

Ile Tyr Thr Leu Arg Asn Lys Asp Met Lys Asp Ala Leu Lys Lys Leu
        290                 295                 300

Met Arg Phe His His Lys Ser Thr Lys Ile Lys Arg Asn Cys Lys Ser
305                 310                 315                 320
```

```
<210> SEQ ID NO 3
<211> LENGTH: 927
<212> TYPE: DNA
<213> ORGANISM: Homo sapiens

<400> SEQUENCE: 3
atggctgaag aaaatcatac catgaaaaat gagtttatcc tcacaggatt tacagatcac    60
cctgagctga agactctgct gtttgtggtg ttctttgcca tctatctgat caccgtggtg   120
gggaatatta gtttggtggc actgatattt acacaccgtc ggcttcacac accaatgtac   180
atctttctgg gaaatctggc tcttgtggat tcttgctgtg cctgtgctat taccccaaa    240 atgttagaga acttcttttc tgagaacaaa aggatttccc tctatgaatg tgcagtacag   300 ttttatttc tttgcactgt ggaaactgca gactgctttc ttctggcagc aatggcctat   360
gaccgctatg tggccatatg caaccccactg cagtaccaca tcatgatgtc caagaaactc   420
tgcattcaga tgaccacagg ggccttcata gctggaaacc tgcattccat gattcatgta   480
gggcttgtat ttaggttagt tttctgtgga tcgaatcaca tcaaccactt ttactgtgat   540
attcttccct tgtatagact ctcttgtgtt gatccttata tcaatgaact ggttctattc   600
atcttctcag gttcagttca agtctttacc ataggtagtg tcttaatatc ttatctctat   660
attcttctta ctattttcaa aatgaaatcc aagagggaa gggccaaagc ttttttctacc   720 tgtgcatccc acttttgtc agtttcatta ttctatggat ctcttttctt catgtacgtt   780
agaccaaatt tgcttgaaga aggggataaa gatataccag ctgcaatttt atttacaata   840
gtagttccct tactaaatcc tttcatttat agcctgagaa atagggaagt aataagtgtc   900
ttaagaaaaa ttctgatgaa gaaataa                                        927
```

```
<210> SEQ ID NO 4
<211> LENGTH: 308
<212> TYPE: PRT
<213> ORGANISM: Homo sapiens
```

<400> SEQUENCE: 4

```
Met Ala Glu Glu Asn His Thr Met Lys Asn Glu Phe Ile Leu Thr Gly
1               5                   10                  15
Phe Thr Asp His Pro Glu Leu Lys Thr Leu Leu Phe Val Val Phe Phe
            20                  25                  30
Ala Ile Tyr Leu Ile Thr Val Val Gly Asn Ile Ser Leu Val Ala Leu
        35                  40                  45
Ile Phe Thr His Arg Arg Leu His Thr Pro Met Tyr Ile Phe Leu Gly
    50                  55                  60
Asn Leu Ala Leu Val Asp Ser Cys Cys Ala Cys Ala Ile Thr Pro Lys
65                  70                  75                  80
Met Leu Glu Asn Phe Phe Ser Glu Asn Lys Arg Ile Ser Leu Tyr Glu
                85                  90                  95
Cys Ala Val Gln Phe Tyr Phe Leu Cys Thr Val Glu Thr Ala Asp Cys
            100                 105                 110
Phe Leu Leu Ala Ala Met Ala Tyr Asp Arg Tyr Val Ala Ile Cys Asn
        115                 120                 125
Pro Leu Gln Tyr His Ile Met Met Ser Lys Lys Leu Cys Ile Gln Met
    130                 135                 140
Thr Thr Gly Ala Phe Ile Ala Gly Asn Leu His Ser Met Ile His Val
145                 150                 155                 160
Gly Leu Val Phe Arg Leu Val Phe Cys Gly Ser Asn His Ile Asn His
                165                 170                 175
Phe Tyr Cys Asp Ile Leu Pro Leu Tyr Arg Leu Ser Cys Val Asp Pro
            180                 185                 190
Tyr Ile Asn Glu Leu Val Leu Phe Ile Phe Ser Gly Ser Val Gln Val
        195                 200                 205
Phe Thr Ile Gly Ser Val Leu Ile Ser Tyr Leu Tyr Ile Leu Leu Thr
    210                 215                 220
Ile Phe Lys Met Lys Ser Lys Glu Gly Arg Ala Lys Ala Phe Ser Thr
225                 230                 235                 240
Cys Ala Ser His Phe Leu Ser Val Ser Leu Phe Tyr Gly Ser Leu Phe
                245                 250                 255
Phe Met Tyr Val Arg Pro Asn Leu Leu Glu Glu Gly Asp Lys Asp Ile
            260                 265                 270
Pro Ala Ala Ile Leu Phe Thr Ile Val Val Pro Leu Leu Asn Pro Phe
        275                 280                 285
Ile Tyr Ser Leu Arg Asn Arg Glu Val Ile Ser Val Leu Arg Lys Ile
    290                 295                 300
Leu Met Lys Lys
305
```

<210> SEQ ID NO 5
<211> LENGTH: 936
<212> TYPE: DNA
<213> ORGANISM: Homo sapiens

<400> SEQUENCE: 5

```
atggggactg gaaatgacac cactgtggta gagtttactc ttttgggggtt atctgaggat    60
actacagttt gtgctatttt atttcttgtg tttctaggaa tttatgttgt caccttaatg   120
ggtaatatca gcataattgt attgatcaga agaagtcatc atcttcatac acccatgtac   180
attttcctct gccatttggc ctttgtagac attgggtact cctcatcagt cacacctgtc   240
atgctcatga gcttcctaag gaaagaaacc tctctccctg ttgctggttg tgtggcccag   300
```

-continued

```
ctctgttctg tagtgacgtt tggtacggcc gagtgcttcc tgctggctgc catggcctat    360
gatcgctatg tggccatctg ctcacccctg ctctactcta cctgcatgtc ccctggagtc    420
tgcatcatct tagtgggcat gtcctacctg ggtggatgtg tgaatgcttg gacattcatt    480
ggctgcttat taagactgtc cttctgtggg ccaaataaag tcaatcactt tttctgtgac    540
tattcaccac ttttgaagct tgcttgttcc catgatttta cttttgaaat aattccagct    600
atctcttctg gatctatcat ctgtggccact gtgtgtgtca tagccatatc ctacatctat    660
atcctcatca ccatcctgaa gatgcactcc accaagggcc gccacaaggc cttctccacc    720
tgcacctccc acctcactgc agtcactctg ttctatggga ccattacctt catttatgtg    780
atgcccaagt ccagctactc aactgaccag aacaaggtgg tgtctgtgtt ctacaccgtg    840
gtgattccca tgttgaaccc cctgatctac agcctcagga caaggagat taaggggct     900
ctgaagagag agcttagaat aaaaatattt tcttga                              936
```

<210> SEQ ID NO 6
<211> LENGTH: 311
<212> TYPE: PRT
<213> ORGANISM: Homo sapiens

<400> SEQUENCE: 6

```
Met Gly Thr Gly Asn Asp Thr Thr Val Glu Phe Thr Leu Leu Gly
1               5                  10                  15

Leu Ser Glu Asp Thr Thr Val Cys Ala Ile Leu Phe Leu Val Phe Leu
                20                  25                  30

Gly Ile Tyr Val Val Thr Leu Met Gly Asn Ile Ser Ile Val Leu
            35                  40                  45

Ile Arg Arg Ser His His Leu His Thr Pro Met Tyr Ile Phe Leu Cys
        50                  55                  60

His Leu Ala Phe Val Asp Ile Gly Tyr Ser Ser Val Thr Pro Val
65                  70                  75                  80

Met Leu Met Ser Phe Leu Arg Lys Glu Thr Ser Leu Pro Val Ala Gly
                85                  90                  95

Cys Val Ala Gln Leu Cys Ser Val Val Thr Phe Gly Thr Ala Glu Cys
            100                 105                 110

Phe Leu Leu Ala Ala Met Ala Tyr Asp Arg Tyr Val Ala Ile Cys Ser
        115                 120                 125

Pro Leu Leu Tyr Ser Thr Cys Met Ser Pro Gly Val Cys Ile Ile Leu
    130                 135                 140

Val Gly Met Ser Tyr Leu Gly Gly Cys Val Asn Ala Trp Thr Phe Ile
145                 150                 155                 160

Gly Cys Leu Leu Arg Leu Ser Phe Cys Gly Pro Asn Lys Val Asn His
                165                 170                 175

Phe Phe Cys Asp Tyr Ser Pro Leu Leu Lys Leu Ala Cys Ser His Asp
            180                 185                 190

Phe Thr Phe Glu Ile Ile Pro Ala Ile Ser Ser Gly Ser Ile Ile Val
        195                 200                 205

Ala Thr Val Cys Val Ile Ala Ile Ser Tyr Ile Tyr Ile Leu Ile Thr
    210                 215                 220

Ile Leu Lys Met His Ser Thr Lys Gly Arg His Lys Ala Phe Ser Thr
225                 230                 235                 240

Cys Thr Ser His Leu Thr Ala Val Thr Leu Phe Tyr Gly Thr Ile Thr
                245                 250                 255
```

```
Phe Ile Tyr Val Met Pro Lys Ser Ser Tyr Ser Thr Asp Gln Asn Lys
            260                 265                 270

Val Val Ser Val Phe Tyr Thr Val Ile Pro Met Leu Asn Pro Leu
        275                 280                 285

Ile Tyr Ser Leu Arg Asn Lys Glu Ile Lys Gly Ala Leu Lys Arg Glu
        290                 295                 300

Leu Arg Ile Lys Ile Phe Ser
305                 310
```

<210> SEQ ID NO 7
<211> LENGTH: 936
<212> TYPE: DNA
<213> ORGANISM: Homo sapiens

<400> SEQUENCE: 7

```
atgggtagaa gaaataacac aaatgtgcct gacttcatcc ttacgggact gtcagattct      60
gaagaggtcc agatggccct ctttatacta tttctcctga tatacctaat tactatgctg     120
ggcaatgtgg ggatgatatt gataatccgc ctggacctcc agcttcacac tcccatgtat     180
tttttcctta ctcacttgtc atttattgac ctcagttact caactgtcat cacacctaaa     240
accttagcga acttactgac ttccaactat atttccttca tgggctgctt tgcccagatg     300
ttcttttttg tcttcttggg agctgctgaa tgttttcttc tctcatcaat ggcctatgat     360
cgctacgtag ctatctgcag tcctctacgt tacccagtta ttatgccaa aaggctgtgt     420
tgcgctcttg tcactgggcc ctatgtgatt agctttatca actcctttgt caatgtggtt     480
tggatgagca actgcatttt ctgcgactca aatgtagttc gtcactttt ctgcgacacg     540
tctccaattt tagctctgtc ctgcatggac acatacgaca ttgaaatcat gatacacatt     600
ttagctggtt ccaccctgat ggtgtccctt atcacaatat ctgcatccta tgtgtccatt     660
ctctctacca tcctgaaaat taattccact tcaggaaagc agaaagcttt gtctacttgt     720
gcctctcatc tcttgggagt caccatcttt atggaacta tgattttac ttatttaaaa     780
ccaagaaagt cttattcttt gggaagggat caagtggctt ctgttttta tactattgtg     840
attcccatgc tgaatccact catttatagt cttagaaaca agaagttaa aaatgctctc     900
attagagtca tgcagagaag acaggactcc aggtaa                               936
```

<210> SEQ ID NO 8
<211> LENGTH: 311
<212> TYPE: PRT
<213> ORGANISM: Homo sapiens

<400> SEQUENCE: 8

```
Met Gly Arg Arg Asn Asn Thr Asn Val Pro Asp Phe Ile Leu Thr Gly
1               5                   10                  15

Leu Ser Asp Ser Glu Glu Val Gln Met Ala Leu Phe Ile Leu Phe Leu
            20                  25                  30

Leu Ile Tyr Leu Ile Thr Met Leu Gly Asn Val Gly Met Ile Leu Ile
        35                  40                  45

Ile Arg Leu Asp Leu Gln Leu His Thr Pro Met Tyr Phe Phe Leu Thr
    50                  55                  60

His Leu Ser Phe Ile Asp Leu Ser Tyr Ser Thr Val Ile Thr Pro Lys
65                  70                  75                  80

Thr Leu Ala Asn Leu Leu Thr Ser Asn Tyr Ile Ser Phe Met Gly Cys
                85                  90                  95

Phe Ala Gln Met Phe Phe Phe Val Phe Leu Gly Ala Ala Glu Cys Phe
```

```
                100                 105                 110
Leu Leu Ser Ser Met Ala Tyr Asp Arg Tyr Val Ala Ile Cys Ser Pro
            115                 120                 125
Leu Arg Tyr Pro Val Ile Met Ser Lys Arg Leu Cys Cys Ala Leu Val
        130                 135                 140
Thr Gly Pro Tyr Val Ile Ser Phe Ile Asn Ser Phe Val Asn Val Val
145                 150                 155                 160
Trp Met Ser Arg Leu His Phe Cys Asp Ser Asn Val Val Arg His Phe
                165                 170                 175
Phe Cys Asp Thr Ser Pro Ile Leu Ala Leu Ser Cys Met Asp Thr Tyr
            180                 185                 190
Asp Ile Glu Ile Met Ile His Ile Leu Ala Gly Ser Thr Leu Met Val
        195                 200                 205
Ser Leu Ile Thr Ile Ser Ala Ser Tyr Val Ser Ile Leu Ser Thr Ile
    210                 215                 220
Leu Lys Ile Asn Ser Thr Ser Gly Lys Gln Lys Ala Leu Ser Thr Cys
225                 230                 235                 240
Ala Ser His Leu Leu Gly Val Thr Ile Phe Tyr Gly Thr Met Ile Phe
                245                 250                 255
Thr Tyr Leu Lys Pro Arg Lys Ser Tyr Ser Leu Gly Arg Asp Gln Val
            260                 265                 270
Ala Ser Val Phe Tyr Thr Ile Val Ile Pro Met Leu Asn Pro Leu Ile
        275                 280                 285
Tyr Ser Leu Arg Asn Lys Glu Val Lys Asn Ala Leu Ile Arg Val Met
    290                 295                 300
Gln Arg Arg Gln Asp Ser Arg
305                 310

<210> SEQ ID NO 9
<211> LENGTH: 792
<212> TYPE: DNA
<213> ORGANISM: Homo sapiens

<400> SEQUENCE: 9
atgaggattt ttagaccgtg gagactgcgc tgccctgccc tgcacctacc ctcactctcc       60
gtgttctcac taaggtggaa attgccttcc ctcactactg acgagaccat gtgtaaaagc      120
gtgaccacag atgagtggaa gaaagtcttc tatgagaaga tggaggaggc aaagccggct      180
gacagctggg acctcatcat agaccccaac ctcaagcaca atgtgctgag ccctggttgg      240
aagcagtacc tggaattgca tgcttcaggc aggttccact gctcctggtg ctggcacacc      300
tggcagtcgc cctacgtggt catcctcttc cacatgttcc tggaccgcgc ccagcgggcg      360
ggctcggtgc gcatgcgcgt cttcaagcag ctgtgctatg agtgcggcac ggcgcggctg      420
gacgagtcca gcatgctgga ggagaacatc gagggcctgg tggacaacct catcaccagc      480
ctgcgcgagc agtgctacgg cgagcgtggc ggccagtacc gcatccacgt ggccagccgc      540
caggacaacc ggcggcaccg cggagagttc tgcgaggcct gccaggaggg catcgtgcac      600
tggaagccca gcgagaagct gctggaggag gaggcgacca cctacacctt ctcccgggcg      660
cccagcccca ccaagtcgca ggaccagacg ggctcaggct ggaacttctg ctctatcccc      720
tggtgcttgt tttgggccac ggtcctgctg ctgatcatct acctgcagtt ctctttccgt      780
agctccgtat aa                                                           792

<210> SEQ ID NO 10
```

<211> LENGTH: 227
<212> TYPE: PRT
<213> ORGANISM: Homo sapiens

<400> SEQUENCE: 10

```
Met Cys Lys Ser Val Thr Thr Asp Glu Trp Lys Lys Val Phe Tyr Glu
1               5                   10                  15

Lys Met Glu Glu Ala Lys Pro Ala Asp Ser Trp Asp Leu Ile Ile Asp
            20                  25                  30

Pro Asn Leu Lys His Asn Val Leu Ser Pro Gly Trp Lys Gln Tyr Leu
        35                  40                  45

Glu Leu His Ala Ser Gly Arg Phe His Cys Ser Trp Cys Trp His Thr
50                  55                  60

Trp Gln Ser Pro Tyr Val Val Ile Leu Phe His Met Phe Leu Asp Arg
65                  70                  75                  80

Ala Gln Arg Ala Gly Ser Val Arg Met Arg Val Phe Lys Gln Leu Cys
                85                  90                  95

Tyr Glu Cys Gly Thr Ala Arg Leu Asp Glu Ser Ser Met Leu Glu Glu
            100                 105                 110

Asn Ile Glu Gly Leu Val Asp Asn Leu Ile Thr Ser Leu Arg Glu Gln
        115                 120                 125

Cys Tyr Gly Glu Arg Gly Gln Tyr Arg Ile His Val Ala Ser Arg
130                 135                 140

Gln Asp Asn Arg Arg His Arg Gly Glu Phe Cys Glu Ala Cys Gln Glu
145                 150                 155                 160

Gly Ile Val His Trp Lys Pro Ser Glu Lys Leu Leu Glu Glu Ala
                165                 170                 175

Thr Thr Tyr Thr Phe Ser Arg Ala Pro Ser Pro Thr Lys Ser Gln Asp
            180                 185                 190

Gln Thr Gly Ser Gly Trp Asn Phe Cys Ser Ile Pro Trp Cys Leu Phe
        195                 200                 205

Trp Ala Thr Val Leu Leu Leu Ile Ile Tyr Leu Gln Phe Ser Phe Arg
        210                 215                 220

Ser Ser Val
225
```

<210> SEQ ID NO 11
<211> LENGTH: 226
<212> TYPE: PRT
<213> ORGANISM: Homo sapiens

<400> SEQUENCE: 11

```
Met Cys Lys Ser Leu Thr Thr Gly Glu Trp Lys Lys Ile Phe Tyr Glu
1               5                   10                  15

Lys Met Glu Glu Val Lys Pro Ala Asp Ser Trp Asp Leu Ile Met Asp
            20                  25                  30

Pro Asn Leu Gln His Asn Val Leu Ala Pro Gly Trp Lys Gln Tyr Leu
        35                  40                  45

Glu Gln His Ala Ser Gly Arg Phe His Cys Ser Trp Cys Trp His Ser
50                  55                  60

Trp Gln Ser Ser Gln Leu Val Ile Leu Phe His Met Tyr Leu Asp Lys
65                  70                  75                  80

Thr Gln Arg Thr Gly Cys Val Arg Met Arg Val Phe Lys Gln Leu Cys
                85                  90                  95

Tyr Glu Cys Gly Ser Ser Arg Leu Asp Glu Ser Ser Met Leu Glu Glu
            100                 105                 110
```

```
Asn Ile Glu Gly Leu Val Asp Asn Leu Val Cys Ser Leu Arg Glu Gln
        115                 120                 125

Cys Tyr Gly Glu Asn Gly Gly Gln Tyr Arg Ile His Val Ala Ser Arg
        130                 135                 140

Gln Asp His Gln Arg His Arg Gly Glu Phe Cys Glu Ala Cys Arg Leu
145             150                 155                 160

Gly Ile Thr His Trp Lys Pro Thr Glu Lys Met Leu Glu Glu Glu Ala
                165                 170                 175

Ser Thr Tyr Thr Phe Ser Arg Pro Ala Asn Pro Ser Lys Thr Ala Asp
            180                 185                 190

Ser Gly Phe Ser Cys Asp Phe Cys Ser Leu Pro Trp Cys Met Phe Trp
        195                 200                 205

Ala Thr Val Leu Leu Leu Ile Ile Tyr Leu Gln Ile Ser Phe Gly Asn
        210                 215                 220

Pro Val
225
```

METHOD FOR IDENTIFYING A MALODOR INHIBITOR

REFERENCE TO SEQUENCE LISTING SUBMITTED ELECTRONICALLY

The content of the electronically submitted substitute sequence listing, file name 2537_094001_SequenceListing_ST25.txt, size 21,771 bytes; and date of creation Mar. 5, 2014, filed herewith, is incorporated herein by reference in its entirety.

FIELD OF THE INVENTION

The present invention relates to a method for identifying a malodor inhibitor.

BACKGROUND OF THE INVENTION

In our living environment, there are a large number of malodorous molecules having different polarization characteristics and molecular weights. Hitherto, a variety of methods have been developed for reducing various malodorous molecules. Generally, the methods for reducing malodors are broadly classified into a biological method, a chemical method, a physical method, or a sensory method. Among malodorous molecules, short-chain fatty acids and amines, having high polarity, can be reduced through a chemical method; i.e., neutralization. Sulfur-containing compounds such as thiol can be reduced through a physical method; i.e., adsorption. However, there still remain many malodorous molecules, such as medium-chain and long-chain fatty acids and skatole, which cannot be reduced through known malodor reducing techniques.

In our everyday lives, among other malodors, fecal odor and foul breath are a particularly unpleasant odor. One of the main causal ingredients of such malodors is skatole. Known means for reducing a skatole odor or a fecal odor include the following: a composition containing a porous substance, an aminopolycarboxylic acid, and a metal (Patent Document 1); a silk burned product supporting a catalyst such as platinum (Patent Document 2); a deodorant containing, as an active ingredient, allyl heptanoate, ethyl vanillin, methyl dihydrojasmonate, raspberry ketone, or eugenol (Patent Document 3); and use of an aromatic component such as amylcinnamaldehyde, ethyl cinnamate, 2-cyclohexylpropanal (Pollenal II), geranyl acetate, cis-3-hexenyl heptanoate, cis-3-hexenyl hexanoate, 3-methyl-3-butenyl 2,2-dimethylpropionate (Lomilat), methylheptenone, valencene, dimethyltetrahydrobenzaldehyde (Triplal or Ligustral), cis-jasmon, acetylcedrene, benzyl acetate, geraniol, orange recovery flavor, or a plant extract of Dipterocarpaceae (Patent Documents 3 and 4).

According to the aforementioned means, a malodor is reduced by decreasing the amount of target malodorous substance through adsorption/decomposition or by means of an aromatic. However, the combination of adsorption and decomposition of a malodorous substance is not immediately effective, since the decrease of the amount thereof requires a long period of time. Use of an aromatic also has drawbacks in that the odor of the aromatic itself sometimes causes an unpleasant sensation to users, and the aromatic tends to mask odor of substances other than the target malodorous substance.

In mammals including humans, the mechanism for odorant recognition includes binding odorant molecules to olfactory receptors present on olfactory sensory neurons included in the olfactory epithelium, which is present in an upper portion of the nasal cavity, and transmitting the response of the receptors to the central nervous system. It has been reported that, 387 different olfactory receptors are present in human, and the genes encoding these olfactory receptors account for about 3% of the human genome.

Generally, a plurality of olfactory receptors respond to a plurality of odorant molecules. Specifically, one single olfactory receptor responds to a plurality of structurally similar odorant molecules at different affinities, while one single odorant molecule is detected by a plurality of olfactory receptors. It is also reported that a certain odorant molecule which can activate one olfactory receptor serves as an antagonist which inhibits activation of another olfactory receptor. Such combined response of these olfactory receptors leads to recognition of each odor.

Thus, when a first odorant molecule is co-present with a second odorant molecule, in some cases, the response of an olfactory receptor to the first odorant molecule is inhibited by the second odorant molecule. Through the inhibition, the odor of the first odorant molecule recognized by olfactory receptors may vary considerably. This mechanism is called "olfactory receptor antagonism." Odor modulation by olfactory receptor antagonism, which differs in mechanism from a malodor reducing method by adding a perfume, an aromatic, or a like substance to the target odorant, can inhibits recognition specific to a malodor. In addition, the odor of an aromatic causing an unpleasant sensation to users can be prevented. Therefore, odor modulation based on olfactory receptor antagonism is a preferred means for reducing malodor.

In order to attain olfactory receptor antagonism, an olfactory receptor which responds to a target malodorous substance must be determined, and a substance which exhibits an antagonistic effect on an olfactory receptor of the malodorous substance must be identified. However, such identification is not easy. Hitherto, odor evaluation has been carried out through a sensory test by experts. However, the sensory test has problems. These problems include for example, odor-evaluators must be trained, and the throughput of the test is low.

PRIOR ART DOCUMENTS

Patent Documents

[Patent Document 1] JP2002-153545 A
[Patent Document 2] WO 2005/007287
[Patent Document 3] JP2005-296169 A
[Patent Document 4] JP2008-136841 A

SUMMARY OF THE INVENTION

The present invention provides a method for identifying a malodor inhibitor comprising:

adding a test substance and a malodor-causing substance to at least one olfactory receptor selected from the group consisting of OR5P3, OR2W1, OR5K1, OR8H1, and a polypeptide which has 80% or more identity in amino acid sequence to any one of the aforementioned polypeptides;

measuring the response of the olfactory receptor to the malodor-causing substance;

identifying, based on the measured response, the test substance which can suppress the response of the olfactory receptor; and selecting, as a malodor inhibitor, the test substance which can suppress the response of the olfactory receptor.

BRIEF DESCRIPTION OF THE DRAWINGS

[FIG. 2] Graphs each showing the response of an olfactory receptor to skatole at different concentration (error bar: ±SE),

[FIG. 5] A graph showing suppression effects on skatole and Hexanoic acid odor by test substances (n=3, error bar: ±SE), The present invention provides a method for identifying a malodor inhibitor based on the response of an olfactory receptor as an index.

Figure 1:
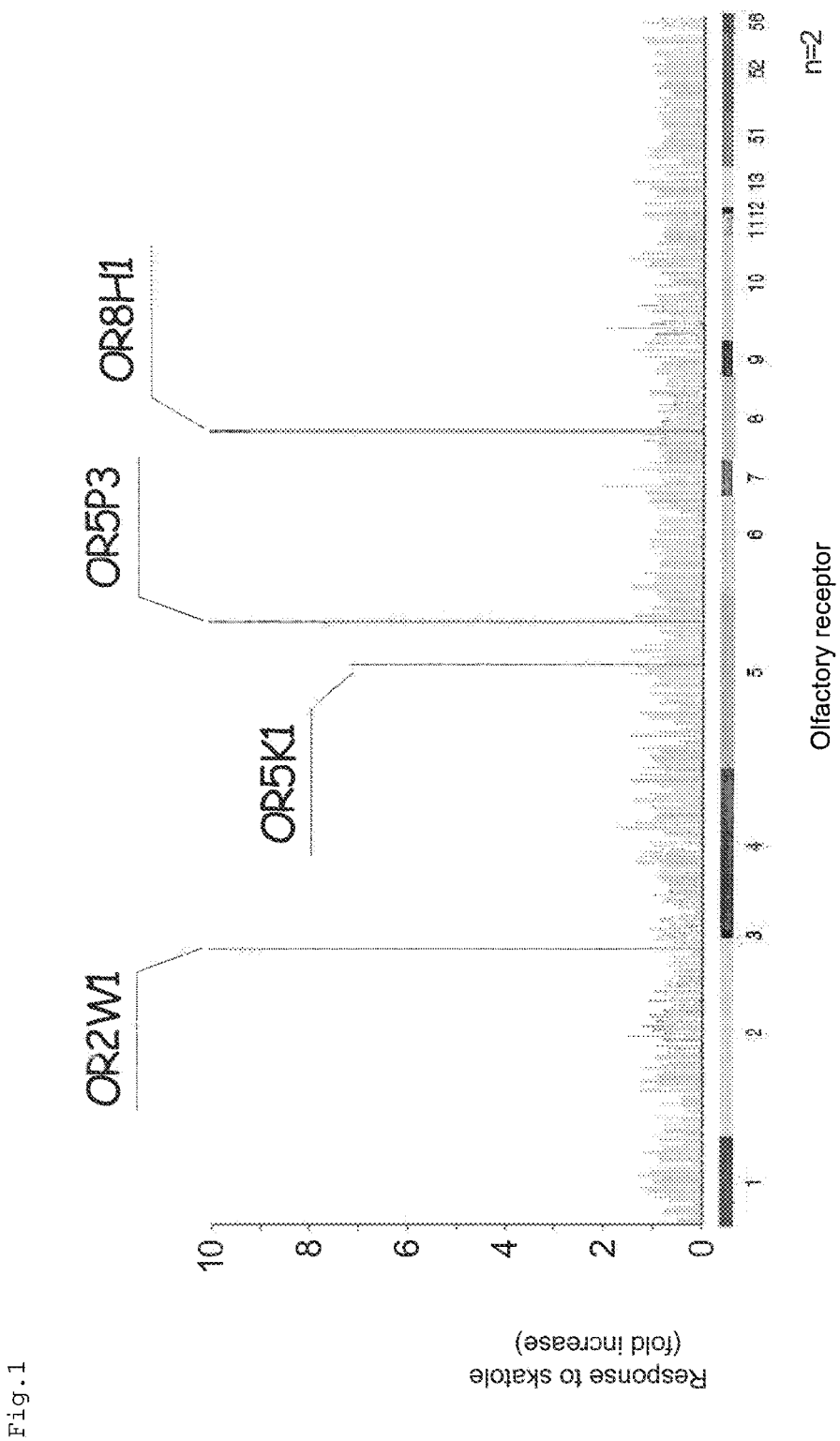
[FIG. 1] A chart showing the responses of olfactory receptors to skatole (X-axis: type of olfactory receptor, Y-axis: response intensity)

The present inventors have successfully determined olfactory receptors which respond to malodor-causing substances such as skatole. The present inventors have found that a substance which can suppress the response of any of the olfactory receptors can be employed as a malodor inhibitor which can suppress a malodor by masking through olfactory receptor antagonism. The present invention has been accomplished on the basis of this finding.

According to the present invention, a malodor inhibitor which can specifically reduce a malodor can be effectively identified, without causing problems which have previously arisen in a conventional malodor reducing method employing a deodorant or an aromatic; e.g., a long time until effectiveness and unpleasant sensation from the odor of the aromatic.

As used herein, the term "masking" in the odor-related field generally refers to means for inhibiting or weakening recognition of a target odor. The term "masking" may encompass chemical means, physical means, biological means, and sensory means. Examples of the masking means include any means for removing a odorant molecule responsible for a target odor from the environment (e.g., adsorption and chemical decomposition of the odorant); means for preventing release of a target odor to the environment (e.g., sealing); and a method in which recognition of a target odor is inhibited by adding another odorant such as a perfume or an aromatic.

As used herein, the term "masking through olfactory receptor antagonism" refers to one embodiment of the aforementioned broadly defined "masking" and is means for inhibiting the response of an olfactory receptor to a target odorant molecule by an additional odorant molecule, to thereby modulate the smell of the target odorant molecule recognized by a subject. Although masking through olfactory receptor antagonism employs an additional odorant molecule, the masking differs from means for canceling out a target odor by use of a strong odorant such as a perfume. In one embodiment of masking through olfactory receptor antagonism, a substance which can inhibit the response of an olfactory receptor such as an antagonist is used. When a response-inhibiting substance which can specifically inhibit the response of a receptor related to recognition of a certain odor is employed, the response of the receptor is suppressed, whereby the odor recognized by a subject can be modulated.

Accordingly, the present invention provides a method for identifying a malodor inhibitor. The method includes: adding a test substance and a malodor-causing substance to at least one olfactory receptor selected from the group consisting of OR5P3, OR2W1, OR5K1, OR8H1, and a polypeptide which has 80% or more identity in amino acid sequence to any one of the aforementioned polypeptides; measuring the response of the olfactory receptor to the malodor-causing substance; identifying, based on the measured response, the test substance which can suppress the response of the olfactory receptor; and selecting, as a malodor inhibitor, the test substance which can suppress the response of the olfactory receptor.

In the method of the present invention, a test substance and a target malodor-causing substance are added to an olfactory receptor which responds to the malodor. The olfactory receptor employed in the method of the present invention may be at least one selected from the group consisting of OR2W1, OR5K1, OR5P3, and OR8H1. OR2W1, OR5K1, OR5P3, and OR8H1 are olfactory receptors each being expressed in human olfactory sensory neurons and are registered in GenBank as GI: 169234788, GI: 115270955, GI: 23592230, and GI: 52353290, respectively.

OR2W1 is a protein encoded by a gene having a nucleotide sequence represented by SEQ ID NO: 1 and consisting of an amino acid sequence represented by SEQ ID NO: 2.

OR5K1 is a protein encoded by a gene having a nucleotide sequence represented by SEQ ID NO: 3 and consisting of an amino acid sequence represented by SEQ ID NO: 4.

OR5P3 is a protein encoded by a gene having a nucleotide sequence represented by SEQ ID NO: 5 and consisting of an amino acid sequence represented by SEQ ID NO: 6.

OR8H1 is a protein encoded by a gene having a nucleotide sequence represented by SEQ ID NO: 7 and consisting of an amino acid sequence represented by SEQ ID NO: 8.

The olfactory receptor employed in the present invention includes a polypeptide which has 80% or more, preferably 85% or more, more preferably 90% or more, still more preferably 95% or more, yet more preferably 98% or more identity in amino acid sequence to any one of the aforementioned OR2W1, OR5K1, OR5P3, and OR8H1. The polypeptide has responsiveness to a malodor-causing substance such as a skatole odor, an indole odor, a fecal odor, or foul breath (e.g., skatole or indole). According to the method of the present invention, the aforementioned olfactory receptors may be used singly or in combination of two or more species. However, the olfactory receptor selected from the group consisting of OR5K1, OR5P3, and OR8H1 is preferably used, and OR5P3 is more preferably used.

Figure 3:
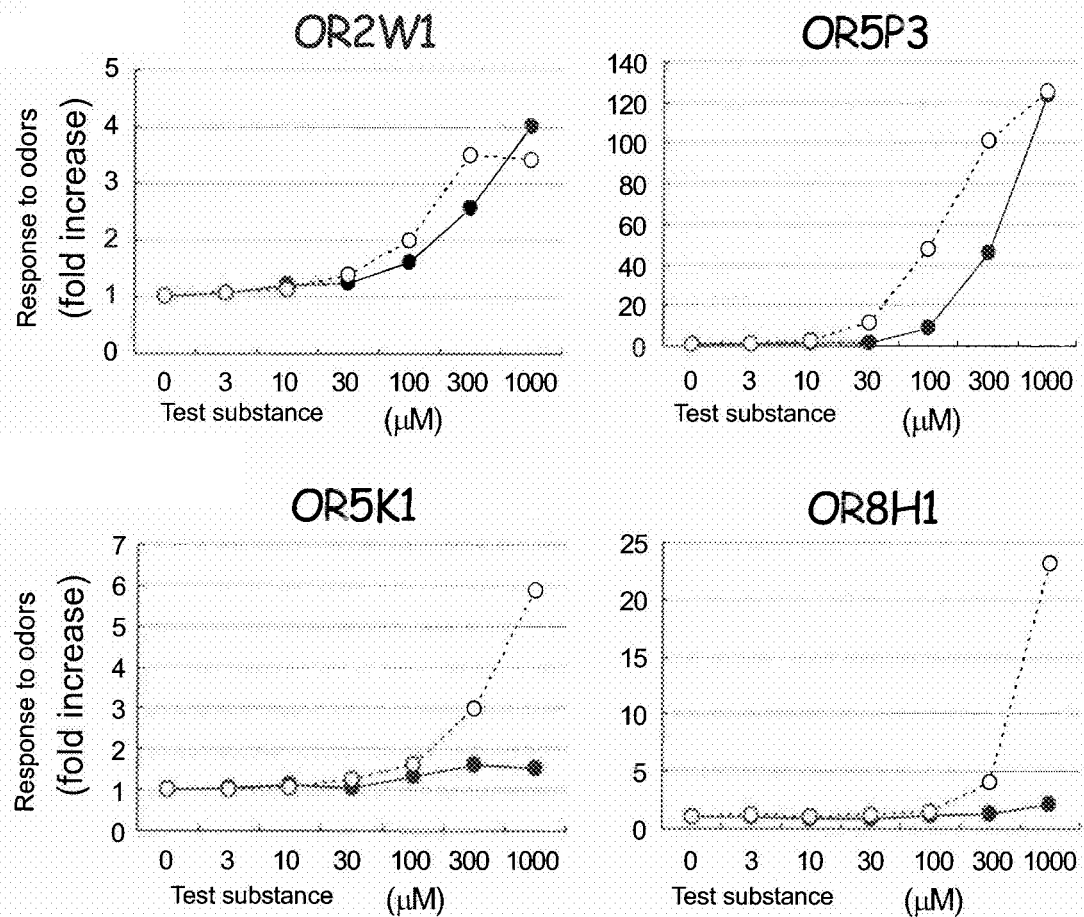
[FIG. 3] Graphs each showing the response of an olfactory receptor to skatole and indole. (filled circle: response to indole, open circle: response to skatole)

As shown in FIGS. 1 to 3, the aforementioned olfactory receptors respond to malodorous substances such as skatole and indole. Therefore, a substance which can suppress the response of such an olfactory receptor can modulate malodor recognition via the central nervous system based on masking through olfactory receptor antagonism, whereby a malodor originating from skatole, indole, or a similar substance can be suppressed. Meanwhile, skatole and indole are generally known odorant molecules causing a malodor such as a fecal odor or foul breath. Thus, the malodor-causing substance employed in the present invention is preferably a fecal odor or foul breath, more preferably skatole or indole. Examples of the malodor suppressed by the malodor inhibitor identified by the method of the present invention include a fecal odor, foul breath, a skatole odor, and an indole odor.

No particular limitation is imposed on the test substance tested in the method of the present invention, so long as the test substance is thought to be used as a malodor inhibitor. The test substance may be a naturally occurring substance or a chemically or biologically synthesized artificial substance. The test substance may be a compound, a composition, or a mixture.

According to the method of the present invention, the test substance and the malodor may be added simultaneously or sequentially in any order.

So long as the function of the olfactory receptor is not impaired, the olfactory receptor may be used in any form in the method of the present invention. For example, the olfactory receptor may be use in the following embodiments: tissues or cells which intrinsically express an olfactory receptor such as olfactory sensory neurons isolated from living bodies and cultured products thereof; olfactory cell membrane bearing the olfactory receptor; recombinant cells genetically modified so as to express the olfactory receptor and cultured products thereof; membrane of the recombinant cells; and artificial lipid bilayer membrane having the olfactory receptor. All of these embodiments are included within the scope of the olfactory receptor used in the present invention.

One preferred embodiment of the present invention employs cells which intrinsically express an olfactory receptor such as olfactory sensory neurons, recombinant cells genetically modified so as to express the olfactory receptor, or a cultured product of any of these. The recombinant cells may be produced through transformation by use of a vector to which a gene encoding the olfactory receptor has been incorporated.

Preferably, in order to promote expression of olfactory receptors in the cell membrane, RTP1S and a target receptor are genetically transfected to cells. An example of RTP1S used in the production of the recombinant cells is human RTP1S. Human RTP1S is registered in GenBank as GI: 50234917, Human RTP1S is encoded by a gene having a nucleotide sequence represented by SEQ ID NO: 9 and is a protein consisting of an amino acid sequence represented by SEQ ID NO: 10, instead of human RTP1S, a polypeptide consisting of an amino acid sequence having 80% or more, preferably 85% or more, more preferably 90% or more, still more preferably 95% or more, yet more preferably 98% or more identity in amino acid sequence to human RTP1S (SEQ ID NO: 10) and which promotes expression of an olfactory receptor in the membrane like human RTP1S may be employed in the present invention. For example, an RTP1S mutant employed in the examples of the specification consisting of an amino acid sequence represented by SEQ ID NO: 11 has 78.9% amino acid sequence identity to the amino acid sequence represented by SEQ ID NO: 10 and can promote expression of an olfactory receptor in the membrane. Thus, the RTP1S mutant is a protein which can be used in production of the aforementioned recombinant cells. Also, mouse RTP1S (Saito H., Chi Q., Zhuang H., Matsunami H., Mainland J. D. Sci, Signal, 2009, 2: ra9) has 89% amino acid sequence identity to the amino acid sequence represented by SEQ ID NO: 10 and can promote expression of an olfactory receptor in the membrane. Thus, mouse RTP1S is a protein which can be used in production of the aforementioned recombinant cells.

In the present invention, the sequence identity (nucleotide sequence and amino acid sequence) is calculated through the Lipman-Pearson method (Science, 227, 1435, (1985)). More specifically, the identity is calculated by a homology analysis program (Search homology) of the genetic information processing software Genetyx-Win (Ver. 5.1.1; Software Development) at a unit size to compare (ktup) of 2

According to the method of the present invention, a test substance and a malodor-causing substance are added to an olfactory receptor, and then the response of the olfactory receptor to the malodor-causing substance is measured. The measurement may be performed through any method known in the art as a response measurement method of olfactory receptors; e.g., the calcium imaging method. When activated by an odorant molecule, an olfactory receptor activates adenylyl cyclase with the aid of Gαs present in cells, to thereby elevate the intracellular cAMP level (Mombaerts P., Nat. Neurosci., 5, 263-278). Therefore, the response of an olfactory receptor can be measured by employing, as an index, the intracellular cAMP level determined after addition of the odorant. The method for determining the cAMP level employed in the present invention includes ELISA, reporter gene assay, and the like.

Subsequently, the suppression effect of the test substance on the response of the olfactory receptor is evaluated on the basis of the measured response of the olfactory receptor, to thereby identify the test substance which can suppress the response. The evaluation of suppression effect can be conducted, for example, by comparing the response of the receptor to the malodor-causing substance measured at different test substance concentrations. As a more specific example, the response to the malodor-causing substance of a higher test substance concentration group and that of a lower test substance concentration group; the response of a test substance addition group and that of a test substance non-addition group; or the response of a group after addition of the test substance and that of the same group before addition of the test substance are compared. In the case where the response of the olfactory receptor is suppressed through addition of the test substance or addition of the test substance at higher concentration, the test substance can be identified as a substance which can suppress the response of the olfactory receptor.

For example, when the olfactory response of a test substance addition group has been suppressed to 80% or less, preferably 50% or less than that of the control group, the test substance may be selected as a malodor inhibitor. In the case where a plurality of olfactory receptors are employed in the method of the present invention, the response of any one of the receptors may be suppressed, but it is preferred that the responses of a plurality of said receptors are suppressed.

The thus-identified test substance is a substance which suppresses the response of the olfactory receptor to the malodor employed in the above procedure, to thereby modulate the malodor recognition at the central nervous system through masking based on olfactory receptor antagonism, causing a subject to disable recognition of the malodor. Thus, the test substance identified in the above procedure is selected as a malodor inhibitor to the malodor employed in the above procedure.

The malodor inhibitor selected in the method of the present invention may be used for suppressing a malodor through olfactory masking based on inhibition of the olfactory receptor of the malodor. Alternatively, the malodor inhibitor may be used for producing a compound or composition for suppressing the malodor. The compound or composition for suppressing the malodor may appropriately contain, in addition to the malodor inhibitor, an additional deodorization ingredient or any ingredient used in a deodorant or a deodorizer, in accordance with the purpose of use. Examples of such ingredients include perfume, powder ingredients, liquid fat and oil, solid fat and oil, wax, hydrocarbon, plant extract, herbal medicines, higher alcohol, lower alcohol, ester, long-chain fatty acid, surfactants (nonionic, anionic, cationic, amphoteric, etc.), sterol, polyol, humectants, water-soluble polymers, thickeners, coating agents, sterilizers, antiseptics, UV-absorbers, fixing agents, cold-sensation agents, hot-sensation agents, stimulators, metal-ion-sequestering agents, sugar, amino acid, organic amine, synthetic resin emulsion, pH-adjusters, anti-oxidants, anti-oxidant aids, oil ingredients, powder, capsules, chelating agents, inorganic salts, organic salt dyes, thickeners, sterilizers, antiseptics, anti-mold agents, colorants, defoaming agents, extenders, modifiers, organic acid, polymer, polymer dispersants, enzymes, and enzyme-stabilizers.

The additional ingredient which can be incorporated into the compound or composition for suppressing the malodor may be any known deodorant having a chemical or physical deodorization effect. Examples of the deodorant include deodorization effective agents extracted from plant leaves, petioles, fruits, stems, roots, and bark (e.g., green tea extract); organic acids such as lactic acid, gluconic acid, succinic acid, glutaric acid, adipic acid, malic acid, tartaric acid, maleic acid, fumaric acid, itaconic acid, citric acid, benzoic acid, and salicylic acid, amino acids, salts thereof, glyoxal, oxidizing agents, flavonoid, catechin, and polyphenol; porous substances such as activated carbon and zeolite; clathrating agents such as cyclodextrin; photocatalysts; and masking agents.

EXAMPLES

The present invention will next be described in more detail by way of examples.

Example 1

Identification of Olfactory Receptors to Malodors (1) Cloning of Human Olfactory Receptor Genes Cloning of human olfactory receptors was performed based on the sequence information registered in GenBank, through PCR with human genomic DNA female (G1521: Promega) as a template. Each of the genes amplified through PCR was inserted into a pENTR vector (Invitrogen) according to an instruction manual. Then, the gene-inserted vector was digested with NotI and AscI, and the obtained fragments were inserted into NotI and AscI sites located downstream of the Flag-Rho tag sequence in the pME18S vector.

(2) Production of pME18S-RTP1S Vector

Cloning of human RTP1S was performed through PCR with a human RTP1 gene (MHS1010-9205862: Open Biosystems) as a template. EcoRI site was added to the forward primer employed in PCR, and XhoI site was added to the reverse primer. A hRTP1S gene (SEQ ID NO: 9) was amplified through PCR and inserted into EcoRI and XhoI site of the pME18S vector.

In a similar manner, instead of the hRTP1S gene (SEQ ID NO: 9), a gene encoding an RTP1S mutant (SEQ ID NO: 11) was inserted into EcoRI and XhoI site of the pME18S vector.

(3) Production of Olfactory Receptor-Expressed Cells

Each of the 369 types of human olfactory receptors was expressed in HEK293 cells. A reaction solution having a composition shown in Table 1 was prepared on a clean bench, and left to stand for 15 minutes. The solution was dispensed to each well of a 96-well plate (BD). Subsequently, HEK293 cells (100 μL, $3 \times 10^5$ cells/cm$^2$) were seeded in each well and cultured for 24 hours in an incubator at 37° C. and under 5% $CO_2$ conditions.

TABLE 1

| | |
|---|---|
| OPTI-MEM (GIBCO) | 50 μL |
| Human olfactory receptor gene (incorporated into pME18S vector in which Flag-Rho tag is added to the N-terminal) | 0.075 μg |
| pGL4.29 (fluc2P-CRE-hygro, Promega) | 0.03 μg |
| pGL4.75 (hRluc-CMV, Promega) | 0.03 μg |
| pME18S-hRTP1S vector or pME18S-RTP1S mutant vector produced in (2) | 0.03 μg |
| Lipofectamine 2000 (Invitrogen) | 0.4 μL |

(4) Luciferase Assay

The olfactory receptor expressed in HEK293 cells activates adenylate cyclase with the aid of Gαs present in cells, to thereby increase intracellular cAMP level. In this study, odorant response was measured by a luciferase reporter gene assay which monitored the intracellular cAMP level as the luminescence value derived from a firefly luciferase gene (fluc2P-CRE-hygro). Also, a Renilla luciferase gene fused downstream of a CMV promoter (hRluc-CMV) was also transfected to HEK293 cells as an internal standard to correct errors in gene transfer efficiency and number of cells.

The culture medium was removed from the culture plate produced in (3) above, and a solution (75 μL) containing an odorant substance (1 mM skatole) in CD293 medium (Invitrogen) was added to each well. Cell culturing was performed for four hours in a $CO_2$-incubator, whereby the luciferase gene sufficiently expressed in the cells. Luciferase activity was measured by means of a Dual-Glo™ luciferase assay system (promega) according to an instruction manual thereof. The luminescence value derived from firefly luciferase induced by odorant stimulation was divided by the luminescence value of cells which were not stimulated with odorants. The thus-obtained—called "fold increase"—was employed as an index for response intensity.

(5) Results

Four olfactory receptors: OR2W1, OR5K1, OR5P3, and OR8H1 exhibited response to skatole (FIG. 1). These are novel skatole receptors whose response to skatole has never been reported.

In Example 1, effective olfactory receptor expression was observed in cells transfected with a RTP1S mutant gene (SEQ ID NO: 11). Such olfactory receptor expression was also observed in cells transfected with an hRTP1S gene (SEQ ID NO: 9). Therefore, the RTP1S transformant (SEQ ID NO: 12) can be employed as a polypeptide which promotes olfactory receptor expression in the cell membrane, instead of hRTP1S (SEQ ID NO: 10).

Example 2

Dose-dependent Response of Skatole Receptor

In a manner similar to that employed in Example 1, each of olfactory receptor OR2W1 (SEQ ID NO: 2), OR5K1 (SEQ ID NO: 4), OR5P3 (SEQ ID NO: 6), and OR8H1 (SEQ ID NO: 8) was expressed with RTP1S mutant (SEQ ID NO: 12) in HEK293 cells. The response of each receptor to skatole (0, 3, 10, 30, 100, 300, and 1000 μM) was determined. As a result, all of the four olfactory receptors exhibited a dose-dependent response to skatole (FIG. 2).

Example 3

Response of Receptor to Skatole and Indole

In a manner similar to that employed in Example 2, the response of each olfactory receptor to skatole and indole (each 0, 3, 10, 30, 100, 300, and 1000 μM) was determined. As a result, these olfactory receptors exhibited a response not only to skatole but also to indole (FIG. 3).

Example 4

Determination of Malodor Receptor Antagonists

Antagonists of the skatole receptors found in Example 1 were identified.

To identify antagonists which can suppress the response of olfactory receptors of skatole, each of 121 test substances (100 μM) was mixed with 300 μM skatole and was applied to HEK293 cells expressing each of OR2W1, OR5K1, OR5P3 and OR8H1.

The response inhibition rate of a test substance was calculated as follows. Firstly, luminescence value derived from firefly luciferase induced by stimulation with skatole (X), and luminescence value in cells which expressed the same receptor but were not stimulated with skatole (Y) were determined. By subtracting Y from X, the receptor activity by stimulation with skatole alone (X−Y) was determined. Similarly, the luminescence value induced by stimulation with a mixture of skatole and a test substance (Z) was determined. Through subtracting Y (the luminescence value in cells which expressed the same receptor but were not stimulated with skatole) from Z, the receptor activity (Z−Y) by stimulation with a mixture of skatole and the test substance was obtained. From the thus-obtained receptor activity by stimulation with skatole alone (X−Y) and the receptor activity in the presence of a test material (Z−Y), the response inhibition rate of the test substance was calculated by the following equation:

Inhibition rate (%) = {1−(Z−Y)/(X−Y)}×100.

In each case, multiple independent experiments were performed in duplicate, and the average of each experiment was used.

As shown in Table 2, we found 43 antagonists of OR8H1, 38 antagonists of OR5K1, 42 antagonists of OR5P3, and 42 antagonists of OR2W1.

TABLE 2

| Test substances | 2W1 | 5K1 | 5P3 | 8H1 |
|---|---|---|---|---|
| 1-(2,3,4,7,8,8a-Hexahydro-3,6,8,8-tetramethyl-1H-3a,7-methanoazulen-5-yl)-ethanone [acetylcedrene] | A | A | A | A |
| Ethyl 2-tert-butyl cyclohexyl carbonate [Flornat] | A | B | A | A |
| 3-Methyl-5-(2,2,3-trimethyl-3-cyclopenten-1-yl)-4-penten-2-ol [Ebanol] | B | A | A | B |
| 1-(5,5-Dimethyl-cyclohexen-1-yl)-4-penten-1-one [Dinascone] | A | B | B | A |
| 1-(2-tert-Butylcyclohexyloxy)-2-butanol [Ambercore] | A | B | B | A |
| Oxacyclohexadecan-2-one [pentalide] | B | B | B | A |
| (Z)-Cycloheptadeca-9-en-1-one [civetone] | A | B | B | B |
| Dodecahydro-3a,6,6,9a-tetramethyl-naphtho[2.1-b]furan [Ambroxane] | A | C | B | A |
| 4-(1,1-Dimethylethyl)-cyclohexanol [p-tert-butlcyclohexanol] | — | A | A | A |
| 1,3,4,6,7,8-Hexahydro-4,6,6,7,8,8-hexamethylcyclopenta-γ-2-benzopyran [Galaxolide] | B | A | C | A |
| 5-Heptyl dihydro-2(3H)-furanone [γ-undecalactone] | B | B | B | B |
| β-Methyl-3-(1-methylethyl)benzenepropanal [Florhydral] | B | B | B | B |
| 3,7-Dimethyl-1-octanol [tetrahydrogenol] | C | B | B | A |
| 5-Methyl-2-(1-methylethyl)-phenol [thymol] | C | A | A | C |
| 1-(2,2-Dimethyl-6-methylen cyclohexyl)-1-penten-3-one [γ-methylionone] | B | B | C | B |
| 3-(1-Ethoxy)-3,7-dimethyl-1,6-octadiene [acetaldehyde ethyl linalyl acetal] | B | B | C | B |
| 4-(2,6,6-Trimethyl-1-cyclohexen-1-yl)-3-buten-2-one [β-ionone] | C | B | — | A |
| Methyl 2-penthyl-3-oxocyclopent-1-yl acetate [methyl dihydrojasmonate] | B | — | B | B |
| 2-Methyl-4-phenylpentanol [Pumple fleur] | — | C | A | B |
| 3,7,11-Trimethyl-1,6,10-dodecatrien-3-ol [nerolidol] | A | — | A | — |
| 7-Methoxy-3,7-dimethyl-octanal [methoxycitronellal] | C | B | C | C |
| 3(Z)-Hexenyl 2-hydroxy benzoate [cis-3-hexynlyl salicylate] | B | C | B | — |
| 1,2,3,4,5,6,7,8-octahydro-8,8-dimethyl-2-naphthaldehyde [Cyclemone A] | B | C | C | C |
| 2-trans-3,7-Dimethyl-2,6-octadien-1-ol [geraniol] | — | C | B | B |
| 3-(4-tert-butylphenyl)propionaldehyde [bourgeonal] | A | B | — | — |
| p-tert-Butyl-α-methyl hydrocinnamic aldehyde [lilial] | C | C | C | C |
| 1-(2,6,6-Trimethyl-3-cyclohexenyl)-2-buten-1-one [δ-damascones] | C | C | C | C |
| 7-Hydroxy-3,7-dimethyl-octanal [hydroxycitronellal] | C | — | B | C |
| Ethyl-2,3-epoxy-3-methyl-3-phenyl propionate | — | C | C | B |
| 8-Cyclohexadecen-1-one [globanone] | A | — | C | — |
| 4-(4-Methyl-3-penten-1-yl)-3-cyclohexene-1-carboxaldehyde [myrac aldehyde] | A | — | — | C |

TABLE 2-continued

| Test substances | 2W1 | 5K1 | 5P3 | 8H1 |
|---|---|---|---|---|
| (Z)-2-(2-Pentenyl)-3-methyl-2-cyclopenten-1-one [cis-jasmone] | B | — | C | C |
| α,α-Dimethyl phenylethyl acetate [dimethylbenzylcarbinyl acetate] | — | C | C | B |
| Hexahydro-4,7-methanoinden-5(6)-yl acetate [tricyclodecenyl acetate] | — | C | C | B |
| 3,7-Dimethyl-6-octen-1-yl acetate [citronellyl acetate] | C | C | — | C |
| 3-Methyl-5-phenyl-1-pentanol [phenylhexanol] | — | — | A | — |
| 3,7-Dimethyl-6-octenal [citronellal] | C | C | C | — |
| 4(3)-(4-Methyl-3-pentenyl)-3-cyclohexenylmethyl acetate [myraldyl acetate] | C | — | C | C |
| Allyl cyclohexylpropionate | C | C | — | C |
| 2,6-Dimethyl-2-octanol/3,7-Dimethyl-3-octanol [tetrahydromugol] | — | C | C | C |
| α-Methyl-4-(2-methylpropyl)-benzenepropanal [suzaral] | C | — | — | B |
| (5E)-3-methylcyclopentadec-5-en-1-one [Muscenone delta] | C | — | C | C |
| Dimethyl-3-cyclohexene-1-carboxaldehyde [Triplal] | C | — | C | C |
| 1,3,3-trimethyl-bicyclo[2.2.1]heptan-2-ol [fenchyl alcohol] | C | — | C | C |
| 2,4,4,7-Tetramethyl-6,8-nonadiene-3-one oxime [Labienoxime] | B | — | — | C |
| 2-Cyclohexylpropanal [Pollenal II] | C | C | C | — |
| n-Hexyl-o-hydroxy benzoate [hexyl salicylate] | B | — | C | — |
| 4-(1-Methylethenyl)-1-cyclohexene-1-carboxyaldehyde [perillaldehyde] | — | C | — | B |

Inhibition rate: A >80%, B >50%, C >20%

Example 5

Sensory Evaluation of Ability of Antagonists for Suppressing Malodor

The abilities of each of the antagonists identified in Example 4 for reducing odor of skatole were investigated through a sensory test.

A cotton ball was put into a glass bottle (Hakuyo. Glass No. 11, capacity: 110 mL), and skatole diluted by 0.001% with propylene glycol (20 µL) and a test substance also diluted by 0.001% (20 µL) were added to the cotton ball. The glass bottle was left to stand for one night at room temperature, to thereby sufficiently evaporate the odorant molecule. The sensory test was performed by four panelists. In the case where skatole alone was added to a glass bottle, the odor intensity was rated to 5. Then, the malodor intensity in the case where skatole and a test substance were added was evaluated with a rating of 0 to 10 (by 0.5) (i.e., 20 ratings)

The following test substances were employed:
  1-(2,3,4,7,8,8a-hexahydro-3,6,8,8-tetramethyl-1H-3a,7-methanoazulen-5-yl)-ethanone (acetylcedrene);
  ethyl 2-tert-butylcyclohexylcarbonate (Floramat (registered trademark));
  oxacyclohexadecan-2-one (pentalide);
  (Z)-cycloheptadeca-9-en-1-one (civetone);
  dodecahydro-3a,6,6,9a-tetramethyl-naphtho[2.1-b]furan (Ambroxane (registered trademark));
  1-(5,5-dimethyl-cyclohexen-1-yl)-4-penten-1-one (Dinascone (registered trademark));
  p-tert-butylcyclohexanol;
  γ-undecalactone;
  β-methyl-3-(1-methylethyl)benzenepropanal (Florhydral (registered trademark));
  3,7-dimethyl-1-octanol (tetrahydrogeraniol);
  1-(2,2-dimethyl-6-methylenecyclohexyl)-1-penten-3-one (γ-methylionone);
  3,7,11-trimethyl-1,6,10-dodecatrien-3-ol (nerolidol);
  3,7-dimethyl-6-octen-1-yl acetate (citronellyl acetate);
  8-cyclohexadecan-1-one (globanone); and
  tricyclodecanyl acetate.

Figure 4:
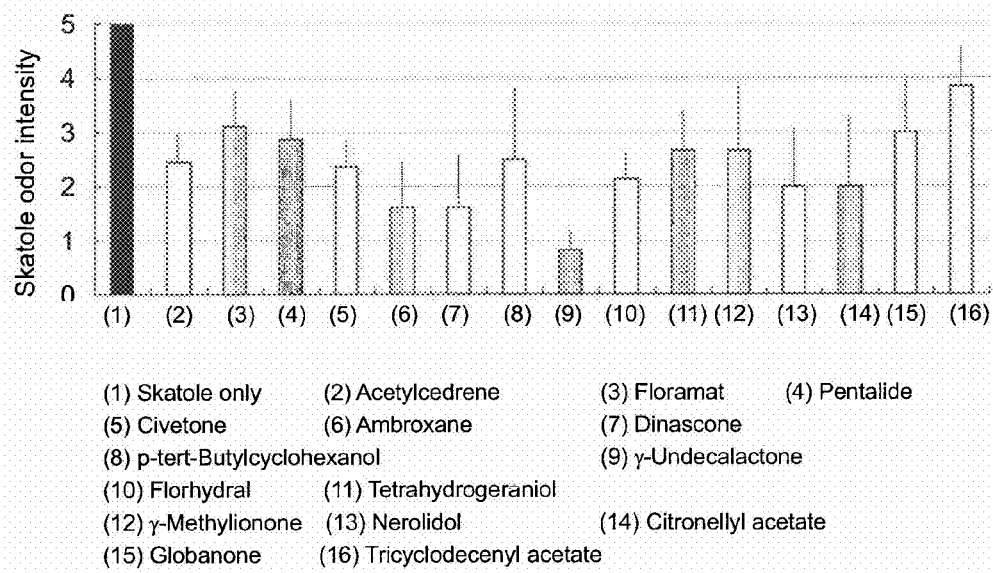
[FIG. 4] A graph showing suppression effects on skatole odor by test substances (n=4, error bar: ±SE).

FIG. 4 shows the results. As is clear from FIG. 4, skatole odor was found to be suppressed in the presence of an antagonist to OR2W1, OR5K1, OR5P3, or OR8H1.

Example 6

Specificity of Malodor Suppression Effect

In order to investigate specificity of malodor suppressing effect of a test substance identified in Example 4, the sensory test was also performed with hexanoic acid, a malodorous compound but structurally differs from skatole. In the experiment, hexanoic acid diluted by 1% with propylene glycol was used as a malodorous compound, and methyl dihydrojasmonate diluted by 1% with propylene glycol was used as a test substance.

As a result, it was found that methyl dihydrojasmonate suppressed skatole odor, did not suppress hexanoic acid odor (FIG. 5). Thus, the malodor suppressing effect by an antagonist was found to be odor-specific.

What is claimed is:

1. A method for identifying a malodor inhibitor comprising:
adding a test substance and a malodor-causing substance to at least one olfactory receptor polypeptide selected from the group consisting of OR5P3, OR2W1, OR5K1, OR8H1, and a polypeptide that has 95% or more identity in amino acid sequence to any one of the aforementioned polypeptides;
measuring the response of the olfactory receptor polypeptide to the malodor-causing substance;
identifying, based on the measured response, a test substance that can suppress the response of the olfactory receptor; and
selecting, as a malodor inhibitor, the test substance that suppresses the response of the olfactory receptor, wherein the malodor is a skatole odor, an indole odor, a fecal odor, or foul breath due to a skatole or indole odor.

2. The method according to claim 1, wherein the malodor is a skatole odor or an indole odor.

3. The method according to claim 1, wherein the at least one olfactory receptor polypeptide is selected from the group consisting of OR5P3, OR5K1, and OR8H1.

4. The method according to claim 1, wherein the olfactory receptor polypeptide is expressed on a cell that can intrinsically express the olfactory receptor polypeptide or on a recombinant cell that is genetically modified so as to express the olfactory receptor polypeptide.

5. The method according to claim 1, which further includes measuring the response of the olfactory receptor polypeptide to which no test substance has been added.

6. The method according to claim 5, wherein, when the response of the olfactory receptor polypeptide to which the test substance has been added is suppressed to 80% or less than the response of the olfactory receptor polypeptide to which no test substance has been added, the test substance is selected as a malodor inhibitor.

7. The method according claim 1, wherein measuring the response of the olfactory receptor polypeptide is performed through a reporter gene assay.

8. The method according to claim 1, wherein the malodor is fecal odor or foul breath due to a skatole or indole odor.

9. The method according to claim 1, wherein at least one of olfactory receptor polypeptide is selected from the group consisting of OR5P3, OR2W1, OR5K1, OR8H1 and a polypeptide that has 98% or more identity in amino acid sequence to any one of the aforementioned polypeptides.

10. The method according to claim 2, wherein the malodor is a skatole odor.

11. The method according to claim 2, wherein the malodor is an indole odor.

12. The method according to claim 8, wherein the malodor is fecal odor.

13. The method according to claim 8, wherein the malodor is foul breath due to a skatole or indole odor.

14. The method according to claim 1, wherein the at least one olfactory receptor polypeptide is OR5P3.

15. The method according to claim 1, wherein the at least one olfactory receptor polypeptide is OR2W1.

16. The method according to claim 1, wherein the at least one olfactory receptor polypeptide is OR5K1.

17. The method according to claim 1, wherein the at least one olfactory receptor polypeptide is OR8H1.

* * * * *